US006284510B1

United States Patent
Ito et al.

(10) Patent No.: US 6,284,510 B1
(45) Date of Patent: Sep. 4, 2001

(54) β-FRUCTOFURANOSIDASE GENE

(75) Inventors: Tetsuya Ito; Koki Fujita; Kozo Hara, all of Yokohama; Takashi Tonozuka; Yoshiyuki Sakano, both of Kunitachi, all of (JP)

(73) Assignee: Society for Techno-innovation of Agriculture, Forestry and Fisheries, Tokyo (JP)

( * ) Notice: Subject to any disclaimer, the term of this patent is extended or adjusted under 35 U.S.C. 154(b) by 0 days.

(21) Appl. No.: 09/503,172

(22) Filed: Feb. 14, 2000

(30) Foreign Application Priority Data

Jun. 8, 1999 (JP) .................................................. 11-160416

(51) Int. Cl.[7] .............................. C12P 21/06; C12N 9/00; C12N 9/24; C12N 1/20; C12N 15/00

(52) U.S. Cl. .......................... 435/200; 435/69.1; 435/183; 435/252.3; 435/320.1

(58) Field of Search ..................................... 435/183, 200, 435/69.1, 252.3, 320.1; 536/23.2

Primary Examiner—Rebecca E. Prouty
Assistant Examiner—Manjunath N. Rao
(74) Attorney, Agent, or Firm—Oblon, Spivak, McClelland, Maier & Neustadt, P.C.

(57) ABSTRACT

A β-fructofuranosidase gene coding for a protein having an amino acid sequence described in Seq. I.D. No. 1 in the Sequence Listing. The gene enables production of β-fructofuranosidase on a large scale more easily and less dependently on the productivity of microorganisms than the production by cultivation of the microorganisms. Also, the β-fructofuranosidase gene is useful for the development of variant enzymes that have increased heat resistance and transfer ratio by means of genetic engineering techniques.

7 Claims, No Drawings

β-FRUCTOFURANOSIDASE GENE

FIELD OF THE INVENTION

The present invention relates to a β-fructofuranosidase gene. β-Fructofuranosidase (EC3.2.1.26.) is an enzyme that hydrolyses sucrose and other β-fructofuranosides to release fructose residue.

This enzyme has an action of transferring a β-fructofuranosyl group from a substrate to water to hydrolyze the substrate. In addition, it has an action of transferring a β-fructofuranosyl group to acceptors having a hydroxyl group such as other saccharides, alcohols, and phenol. Utilizing this action, the enzyme is used in the synthesis of transfructosylated oligosaccharides such as lactosucrose.

BACKGROUND OF THE INVENTION

Transfructosylated oligosaccharides such as lactosucrose have an activity of propagating bifidobacterium and currently attract attention in the fields of foods and drugs as a new sweetener that is a substitute for sucrose.

Transfructofuranosylated oligosaccharide, one of transfructosylated oligosaccharides, is usually produced by allowing β-fructofuranosidase to act on a raw material such as sucrose, starch sugar, lactose, etc.

Microorganisms, such as Arthrobacter, produce β-fructofuranosidase. However, said microorganisms are each low in β-fructofuranosidase productivity. Therefore, there is a problem in that microorganisms must be cultivated in large amounts to produce transfructofuranosylated oligosaccharides on a large scale.

Incidentally, current progress in genetic engineering techniques has made it possible to obtain a large amount of an enzyme relatively easily even if the amino acid sequence of the enzyme has not been elucidated yet. This is achieved by isolating the gene coding for the enzyme, determining the base sequence of the enzyme, producing a recombinant DNA containing the gene coding for the enzyme, incorporating the recombinant DNA into microorganism or animal or plant cells, and cultivating the obtained transformants.

Accordingly, it has been a desire for ascertaining the gene coding for β-fructofuranosidase and determining its base sequence.

SUMMARY OF THE INVENTION

An object of the present invention is to identify the structure of the gene coding for a polypeptide having a β-fructofuranosidase activity, thereby providing a mass production system for a transfructofuranosylated oligosaccharide using the enzyme.

Elucidation of the gene coding for a polypeptide having a β-fructofuranosidase activity is considered to give a possibility for obtaining the enzyme in a large amount. Also, it is considered to be useful for the development of a variant enzyme whose heat resistance and transfer ratio are increased by means of genetic engineering techniques.

The inventors of the present invention have made research on the synthesis of transfructosylated oligosaccharides for several years continuously. During the research, the inventors have made it clear that *Arthrobacter* sp. K-1 strain produces β-fructofuranosidase having substrate specificity that is different from that of other β-fructofuranosidase and that exhibits high transfer efficiency in the presence of an acceptor.

That is, *Arthrobacter* sp. K-1 strain can produce β-fructofuranosidase outside the cell without addition of sucrose to the culture medium and it does not synthesize high molecular fructan. Therefore, it is easy for handling.

Therefore, the present inventors have paid their attention onto the structural gene coding for the β-fructofuranosidase, and have made intensive study. As a result, the inventors have analyzed the structure of the β-fructofuranosidase gene.

The first aspect of the present invention provides a β-fructofuranosidase gene coding for a protein having an amino acid sequence described in Seq. I.D. No. 2 in the Sequence Listing.

DETAILED DESCRIPTION OF THE INVENTION

First, an outline on the approach to the present invention will be described.

β-fructofuranosidase which was obtained from the culture of a bacterium belonging to the genus *Arthrobacter* and having a productivity of β-fructofuranosidase was highly purified and the amino acid sequence of its N-terminal was determined.

Further, the β-fructofuranosidase was enzymatically decomposed to prepare peptide fragments, and their amino acid sequences were determined.

Then, a primer was prepared based on the base sequence confirmed from the amino acid sequence. Using this primer, there was practiced a polymerase chain reaction (PCR) method using the primer and chromosomal DNA extracted from a bacterial strain belonging to the genus *Arthrobacter* as a template to obtain a clear band of 221 bp.

After TA cloning of the obtained PCR product, the base sequence thereof was analyzed using a DNA sequencer. The obtained base sequence was translated to amino acids and homology search was performed to find that it has a high homology with enzymes acting on sucrose. Therefore, the DNA was considered to be a portion of the β-fructofuranosidase gene.

Hence, cloning of the β-fructofuranosidase gene was practiced using the PCR product as a probe.

First, the chromosomal DNA extracted from a bacterium belonging to the genus *Arthrobacter* was digested with restriction enzymes and then subjected to Southern blot hybridization. As a result, the presence of the target β-fructofuranosidase gene which in an about 9 Kbp DNA fragment was confirmed. After cutting out the DNA fragment from the gel and purifying it, the DNA was in vitro packaged in a cosmid vector and a partial DNA library was constructed.

Out of the library was screened *Escherichia coli* having a β-fructofuranosidase gene by colony hybridization. From positive clone was extracted a gene consisting of 1917 bases in total. That is, this gene is the β-fructofuranosidase gene of the present invention.

Hereafter, the present invention will be described in detail.

As described above, the β-fructofuranosidase gene of the present invention is derived from a microorganism of *Arthrobacter* having a β-fructofuranosidase producing ability. Such a microorganism of *Arthrobacter* having a β-fructofuranosidase producing ability includes *Arthrobacter* sp. K-1 strain and variant strains thereof. Any mutants of the present bacterium obtained naturally or by an artificial means are all embraced by the present invention so far as they have the above-described ability.

*Arthrobacter* sp. K-1 strain was isolated from the soil of Osaka prefecture and deposited at National Institute of Bioscience and Human-Technology, Agency of Industrial Science and Technology, Ministry of International Trade and Industry at 1-3 Higashi 1-chome, Tsukuba-shi, Ibaraki-ken 305, JAPAN. The Accession Number is FERM BP-3192. The bacteriological properties of the said bacterium are described in Japanese Patent No. 2781412.

The β-fructofuranosidase can be obtained from the above-mentioned microbial strain. Specifically, after cultivating the above strain in a nutrient medium, microbial cells are removed by centrifugation or the like to recover the culture medium. Subsequently, using purification means such as salting out or various types of column chromatography, a highly purified β-fructofuranosidase can be obtained.

Next, the amino acid sequence of N-terminal of the purified β-fructofuranosidase is determined using a Gas Phase Protein Sequencer "476A" manufactured by Applied Biosystems. The determined amino acid sequence consists of 9 amino acids as shown in Seq. I.D. No. 3 in the Sequence Listing. Further, the β-fructofuranosidase is enzymatically decomposed to prepare peptide fragments and their amino acid sequences are determined (Seq. I.D. Nos. 4 to 6 in the Sequence Listing).

Based on the information on the decoded amino acid sequences, primers areprepared (Seq. I.D. Nos. 7and 8 inthe Sequence Listing). PCR is performed using the primers and the chromosomal DNA extracted from the strain of *Arthrobacter* as a template.

As a result, a DNA amplified product of 221 bp is obtained. This DNA is purified and TA cloned. Thereafter, its base sequence is decoded using a DNA sequencer. The determined base sequence is as shown in Seq. I.D. No. 9 in the Sequence Listing.

The obtained base sequence is translated into amino acids and homology search is conducted. As a result, found is high homology with enzyme acting on a β-fructofuranosyl group in sucrose, etc., such as Levansucrase derived from microorganism of *Acetobacter*. Hence, this DNA is considered to be a part of β-fructofuranosidase.

Then, cloning of full-length gene of β-fructofuranosidase is practiced using the PCR product as a probe.

First, the chromosomal DNA extracted from the strain of *Arthrobacter* is digested with a restriction enzyme and then subjected to Southern blot hybridization. As a result, the presence of the target β-fructofuranosidase gene is confirmed in about 9 Kbp DNA fragment.

The DNA fragment is cut out of the gel and purified. Thereafter, the DNA is in vitro packaged in a cosmid vector to construct a partial DNA library.

Out of the library, *Escherichia coli* having a β-fructofuranosidase gene is screened by colony hybridization and thus a positive clone is obtained. After subcloning the β-fructofuranosidase gene by a conventional method, the base sequence of the β-fructofuranosidase gene is determined.

The β-fructofuranosidase gene of the present invention has the base sequence described in Seq. I.D. No. 1 in the Sequence LisLing. The β-fructofuranosidase gene according to the present invention is an enzyme having a novel amino acid sequence and no protein having a homology therewith of 65% or more has been known to exist.

From this fact, it is clear that the β-fructofuranosidase of the present invention is a gene having a novel base sequence that has never been elucidated yet.

The expression of β-fructofuranosidase can be confirmed by cultivation of *Escherichia coli*, which is the above transformants, and measurement of the enzyme activity of *Escherichia coli* cells and of the supernatant.

The β-fructofuranosidase can be obtained by cultivating the transformants in a nutrient medium, crushing the obtained cells, subjecting the crushed product to solid-liquid separation, and purifying the obtained supernatant by a conventional method.

The production of β-fructofuranosidase utilizing a microorganism such as *Arthrobacter* depends on the productivity of said microorganism and hence it is necessary to cultivate the microorganism in large amounts in order to produce the enzyme on a large scale.

However, expression of the gene of the enzyme elucidated by the present invention makes it possible to produce β-fructofuranosidase on a large scale with ease.

The β-fructofuranosidase thus obtained has succeeded the specific properties of the enzyme produced by *Arthrobacter* sp. K-1 strain as they are and has substrate specificity different from that of ordinary β-fructofuranosidase and further exhibits high transfer efficiency in the presence of an acceptor.

Therefore, the β-fructofuranosidase produced by the gene of the present invention is useful in the efficient production of transfructosylated oligosaccharide that has attracted attention in the fields of foods and drugs.

Also, the gene of the present invention is expected to be useful for the development of variant enzymes having increased heat resistance and transfer ratio by using genetic engineering Lechniques.

According to the present invention, the gene of β-fructofuranosidase is provided.

Expression of the gene of the present invention enables production of β-fructofuranosidase on a large scale more easily and less dependently on the productivity of microorganisms than the production by cultivation of the microorganisms.

The β-fructofuranosidase has different substrate specificity in comparison with ordinary β-fructofuranosidase and exhibits high transfer ratio in the presence of an acceptor.

Therefore, the β-fructofuranosidase produced by use of the gene of the present invention is useful in efficient production of transfructosylated oligosaccharides that are attracting attention in the fields of foods and drugs.

Also, the β-fructofuranosidase gene of the present invention is useful for the development of variant enzymes that have increased heat resistance and transfer ratio by means of genetic engineering techniques.

EXAMPLES

Next, the present invention will be described in detail by examples. However, the present invention is not limited thereto. Example 1

In a 500-ml Sakaguchi flask was charged 100 ml of a liquid medium (pH 7.0) consisting of 4.0% (w/v) of soluble starch, 0.8% (w/v) of polypeptone, 1.2% (w/v) of yeast extract, 0.4% (w/v) of ammonium phosphate, 0.1% (w/v) of magnesium sulfate heptahydrate and water. This was sterilized in an autoclave at 120° C. for 15 minutes and cooled. Thereafter, *Arthrobacter* sp. K-1 strain (FERM BP-3192) was inoculated and the strain was cultivated at 37° C. for 2 days with shaking to obtain a culture.

The culture was centrifuged to obtain a supernatant. To this was added ammonium sulfate to 60% saturation and the mixture was left to stand overnight at 4° C. Thereafter, the mixture was centrifuged and the precipitates containing β-fructofuranosidase were collected. The precipitates were dissolved in 50-mM phosphate buffer solution (pH 7.0) and the solution was dialyzed against fresh solution of the same buffer solution for one day and night. Thereafter, the solution was centrifuged and the supernatant was collected.

The supernatant was loaded in a column packed with 100 ml of "DEAE-Toyopearl 650M", a gel for ion exchange chromatography, manufactured by Tosoh Corp. preliminarily equilibrated with a 20-mM phosphate buffer solution (pH7.0). Eluting with sodium chloride whose concentration was increased linearly from 0 M to 0.5 M and the fractions having β-fructofuranosidase activity were recovered.

The fractions were dialyzed against a 20-mM phosphate buffer solution (pH 7.0) containing 2-M ammonium sulfate and then centrifuged to recover a supernatant. The supernatant was loaded in a column packed with 100 ml of "Butyl Toyopearl 650M", a gel for hydrophobic column chromatography, manufactured by Tosoh Corp., preliminarily equilibrated with 20-mM phosphate buffer solution (pH7.0) containing 1-M ammonium sulfate. Passing a 20-mM phosphate buffer solution through the column under a linearly decreasing concentration gradient of 1 M to 0 M of ammonium sulfate, the fractions having β-fructofuranosidase activity were recovered.

Thereafter, the fractions were dialyzed against a 20-mM phosphate buffer solution (pH 7.0) and loaded in a column packed with "SephadexG-75", agel for gel filtration column chromatography, manufactured by Pharmacia, preliminarily equilibrated with a 20-mM phosphate buffer solution (pH 7.0). Thus, the fractions having β-fructofuranosidase activity were recovered. This was named purified enzyme. Upon conducting SDS-polyacrylamide gel electrophoresisof the purified β-fructofuranosidase, asingle band was observed.

After conducting 10% SDS-polyacrylamide electrophoresis of the purified β-fructofuranosidase, the protein in the gel was transferred to PVDF Membrane "IMMOBILON-P" manufactured by Millipore. The band of β-fructofuranosidase transferred onto the PVDF Membrane was cut out and analyzed by a conventional method using Gas Phase Protein Sequencer "476A" manufactured by Applied Biosystems. As a result, it revealed that the enzyme had the amino acid sequence shown in Seq. I.D. No. 2 in the Sequence Listing at the N-terminal thereof.

Further, about 2.5 μg of the purified β-fructofuranosidase was subjected to 10% SDS-polyacrylamide gel electrophoresis and stained. Thereafter, the band of β-fructofuranosidase was cut out and inserted in a well of 15% SDS-polyacrylamide gel electrophoresis. Thereon was overlaid V8 protease derived from *Staphylococcus aureus* in an amount of 1/1,000 (w/w) based on the weight of the protein and electrophoresis was performed.

After confirming that the bands of β-fructofuranosidase and V8 protease were concentrated in a concentrated gel, the electrophoresis was temporarily stopped and treatment with protease was conducted at room temperature for 1 hour.

Thereafter, the electrophoresis was started again and three kinds of peptide fragments of β-fructofuranosidase were isolated. Amino acid sequence analysis performed in the same manner as above revealed that the peptide fragments had amino acid sequences shown in Seq. I.D. Nos. 4 to 6 in the Sequence Listing.

Out of the decoded N-terminal amino acid sequence, a region where less codon degeneration occurred was selected and a sense primer (Seq. I.D. No. 7 in the Sequence Listing) was prepared. Also, a region where less codon degeneration occurred was selected out of the inner amino acid sequence to prepare an anti-sense primer (Seq. I.D. No. 8 in the Sequence Listing).

On the other hand, the chromosomal DNA was extracted from *Arthrobacter* sp. K-1 strain (FERM BP-3192) as follows.

First, in 500-ml Sakaguchi flasks were each charged 100 ml of a liquid medium (pH 7.0) consisting of 4.0% (w/v) of soluble starch, 0.8 (w/v) of polypeptone, 1.2% (w/v) of yeast extract, 0.4% (w/v) of ammonium phosphate, 0.1% (w/v) of magnesium sulfate heptahydrate and water, and the flasks were autoclaved at 120° C. for 20 minutes to sterilize them and then cooled. Thereafter, *Arthrobacter* sp. K-1 strain was inoculated to the medium in each flask and cultivated at 37° C. for 48 hours with shaking.

The culture was centrifuged to separate the cells, which then were frozen at −80° C. Thereafter, cooled SET buffer solution (pH 8.0) was added and the mixture was stirred sufficiently. To this solution were added 0.1% (w/v) of lysozyme and 0.05% (w/v) of ribonuclease and the mixture was allowed to react at 37° C.

After completion of the bacteriolysis, 0.1 ml of 10% SDS was added and then proteinase K (Sigma) was added to a final concentration of 100 μg/ml. The mixture was allowed to react for over one night at 50° C. After completion of the reaction, a mixed liquid of chloroform/isoamyl alcohol was added to extract chromosomal DNA. To the extract was added cooled ethanol and the DNA occurring on the interface was scraped using a glass rod and the DNA was dissolved in TE buffer solution (pH 7.0).

PCR (25 cycles of 94° C. for 1 minute, 55° C. for 1 minute, and 72° C. for 2 minutes) was conducted using the above prepared primers and the chromosomal DNA of *Arthrobacter* sp. K-1 strain as a template in a DNA Thermal Cycler manufactured by Perkin Elmer to amplify the β-fructofuranosidase gene fragments. As a result, agarose gel electrophoresis ascertained a DNA band of 221 bp.

The DNA band was cut out of the gel and then purified using DNA PREP KIT manufactured by Diatron.

The DNA was ligated with pT7 Blue T-vector manufactured by Novogen and was used to transform *Escherichia coli* JM109. From the transformed *Escherichia coli* was purified plasmid and its base sequence was determined using DNA Sequencing System "377" manufactured by Applied Biosystems. As a result, the base sequence described in Seq. I.D. No. 8 in the Sequence Listing was obtained.

The DNA was translated into amino acids and homology search was performed. As a result, high homology was found with enzyme acting on a β-fructofuranosyl group in sucrose, etc., such as Levansucrase derived from *Acetobacter*. Hence, this DNA was considered to be a part of β-fructofuranosidase gene.

Then, cloning of β-fructofuranosidase gene was practiced using the PCR product as a probe.

First, the chromosomal DNA extracted from a bacterium belonging to the genus *Arthrobacter* was digested with various restriction enzymes and then subjected to Southern blot hybridization. As a result, it was confirmed that the target β-fructofuranosidase gene was present in an about 9 Kbp DNA fragment obtained by cleavage of the chromosomal DNA with BamH I. The DNA fragment around this was cut out of the gel and purified. Thereafter, the DNA was inserted into the BamH I site of cosmid vector Charomid 9–36 manufactured by Nippon Gene.

This vector was packaged using Giga Pack III Gold in vitro Packaging Kit manufactured by Stratagene to construct a partial DNA library. Next, the packaged recombinant phage was infected to *Escherichia coli* JM109 and *Escherichia coli* having the β-fructofuranosidase gene was screened by colony hybridization.

The positive clones identified by primary screening were completely separated by conducting secondary and tertiary screenings. The β-fructofuranosidase gene in the obtained positive clones was subcloned in pUC119 by a conventional manner and then the base sequence of the β-fructofuranosidase gene was determined.

The β-fructofuranosidase gene of the present invention has the base sequence described in Seq. I.D. No. 1 in the Sequence Listing. The β-fructofuranosidase gene according to the present invention is a polypeptide having a novel amino acid sequence and no protein has been known to exist that has a homology therewith of 65% or more.

Upon comparing the β-fructofuranosidase gene having the amino acid sequence shown in Seq. I.D. No. 1 in the Sequence Listing with the amino acid sequences previously known, the amino acid sequence of the N-terminal of the β-fructofuranosidase (Seq. I.D. No. 2 in the Sequence Listing) coincided with the sequence of Nos. 1 to 9 amino acids in the sequence shown in Seq. I.D. No. 1 in the Sequence Listing.

Further, the sequences of the peptide fragments derived from the β-fructofuranosidase (Seq. I.D. Nos. 3, 4 and 5 in the Sequence Listing) were coincided with the sequences of 278th to 287th, 320th to 328th, and 70th to 79th, respectively in the amino acid sequence shown in Seq. I.D. No. 1 in the Sequence Listing.

Therefore, the sequence of from −36th to −1st in the amino acid sequence shown in Seq. I.D. No. 1 in the Sequence Listing is presumed to be a signal peptide region generally recognized in secretor enzymes.

From the above results, the enzyme of this example was confirmed to have the amino acid sequence shown in Seq. I.D. No. 2 in the Sequence Listing and to be encoded by the DNA having the base sequence shown in Seq. I.D. No. 1 in the Sequence Listing.

What is claimed is:

1. An isolated polynucleotide encoding a β-fructofuranosidase protein having an amino acid sequence described in Seq. I.D. No. 2 in the Sequence Listing.

2. The isolated polynucleotide of claim 1, wherein said protein is derived from microorganism belonging to genus *Arthrobacter*.

3. The isolated polynucleotide of claim 2, wherein the microorganism is *Arthrobacter* sp. K-1 (FERM BP-3192).

4. The isolated polynucleotide of claim 1 comprising the sequence in SEQ ID NO:1.

5. A vector comprising the isolated polynucleotide of claim 1.

6. A microorganism comprising the isolated polynucleotide of claim 1.

7. A method of producing a β-fructofuranosidase comprising culturing the microorganism of claim 6 in a nutrient medium which allows expression of the isolated polynucleotide; and collecting the β-fructofuranosidase.

* * * * *

SEQUENCE LISTING

```
<160> NUMBER OF SEQ ID NOS:  9

<210> SEQ ID NO 1
<211> LENGTH: 1917
<212> TYPE: DNA
<213> ORGANISM: Arthrobacter sp.
<220> FEATURE:
<221> NAME/KEY: CDS
<222> LOCATION: (181)..(1917)
<221> NAME/KEY: mat_peptide
<222> LOCATION: (289)..(1917)

<400> SEQUENCE: 1
cggcgaactc ttcctcgttc cacggctcgt cgagttagca gggttgtcaa gttccgcgag      60
cgatgcagta gccgcggcga ccatgtcccc cgaaatacct acaaacctat gcgttgtctt     120
atgagagcat gtagaggtgc aaatcgattt gcataccttt cccacatgaa ggagagcacg     180 atg act cac tcg acg aga ggg cgc gtt cgt cgc gtc ctg gcc gga ggg      228
Met Thr His Ser Thr Arg Gly Arg Val Arg Arg Val Leu Ala Gly Gly
    -35                 -30                 -25 ctg gcg acc agt acc ctt gcg gcc gcc gtc ctg atc gcc gga gcc gcc      276
Leu Ala Thr Ser Thr Leu Ala Ala Ala Val Leu Ile Ala Gly Ala Ala
-20                 -15                 -10                  -5 cct gcg act gct cag tca ggg ctc cag gac ggc ccg gag ccg aca att      324
Pro Ala Thr Ala Gln Ser Gly Leu Gln Asp Gly Pro Glu Pro Thr Ile
             -1   1               5                  10 cac act cag cag gcg tac gcc ccc gag gat gat ttc acc gcc aag tgg      372
His Thr Gln Gln Ala Tyr Ala Pro Glu Asp Asp Phe Thr Ala Lys Trp
            15                  20                  25 aca cgc gcc gac gcc cgc cag ttg cag cgc atg tcc gac ccc acc gcg      420
Thr Arg Ala Asp Ala Arg Gln Leu Gln Arg Met Ser Asp Pro Thr Ala
        30                  35                  40 ccg tcg cgc gag aac tcg atg ccg gcg tcc gtc acc atg cca act gtg      468
Pro Ser Arg Glu Asn Ser Met Pro Ala Ser Val Thr Met Pro Thr Val
 45                  50                  55                  60 ccg cag gac ttc ccg gac atg tcc aac gag cag gtg tgg gtg tgg gac      516
Pro Gln Asp Phe Pro Asp Met Ser Asn Glu Gln Val Trp Val Trp Asp
                     65                  70                  75 acc tgg ccg ctg acg gat gag gat gcc aac cag tac tcc gtc aat ggc      564
Thr Trp Pro Leu Thr Asp Glu Asp Ala Asn Gln Tyr Ser Val Asn Gly
             80                  85                  90
```

-continued

| | | |
|---|---|---|
| tgg gag atc atc ttc tcg ctg gtg gcc gac cgc aac ctc ggc ttt gac<br>Trp Glu Ile Ile Phe Ser Leu Val Ala Asp Arg Asn Leu Gly Phe Asp<br>    95                 100                 105 | | 612 |
| gac cgg cac gtg ttc gcg aag atc ggc tac ttc tac cgt ccc gcc ggc<br>Asp Arg His Val Phe Ala Lys Ile Gly Tyr Phe Tyr Arg Pro Ala Gly<br>110                 115                 120 | | 660 |
| gta ccg gcg gca gag cgt ccc gag aac ggc ggc tgg acg tat ggc ggg<br>Val Pro Ala Ala Glu Arg Pro Glu Asn Gly Gly Trp Thr Tyr Gly Gly<br>125                 130                 135                 140 | | 708 |
| ctg gtg ttc aag gaa ggc gtc acc ggc cag atc ttc gag gat cag tcg<br>Leu Val Phe Lys Glu Gly Val Thr Gly Gln Ile Phe Glu Asp Gln Ser<br>                145                 150                 155 | | 756 |
| ttc agc cac cag acc cag tgg tcg ggg tcg gcg cgt gtg tcc aag aac<br>Phe Ser His Gln Thr Gln Trp Ser Gly Ser Ala Arg Val Ser Lys Asn<br>                160                 165                 170 | | 804 |
| ggc gag atc aag ctg ttc ttc acc gac gtc gcg ttc tac cgc aac tct<br>Gly Glu Ile Lys Leu Phe Phe Thr Asp Val Ala Phe Tyr Arg Asn Ser<br>                175                 180                 185 | | 852 |
| gac ggc acg aac atc aag ccc tat gac ccc cgc atc gcg ctg agc gtc<br>Asp Gly Thr Asn Ile Lys Pro Tyr Asp Pro Arg Ile Ala Leu Ser Val<br>190                 195                 200 | | 900 |
| ggc aag gtg aag gcg aac aag aag ggc gtc acc ctc act ggt ttc aat<br>Gly Lys Val Lys Ala Asn Lys Lys Gly Val Thr Leu Thr Gly Phe Asn<br>205                 210                 215                 220 | | 948 |
| aag gtg acc gac ctg ctg cag gcg gac ggc acg tat tac cag acg ggg<br>Lys Val Thr Asp Leu Leu Gln Ala Asp Gly Thr Tyr Tyr Gln Thr Gly<br>                225                 230                 235 | | 996 |
| gcg cag aac gag ttc ttc aac ttc cgc gac ccg ttc acc ttc gag gac<br>Ala Gln Asn Glu Phe Phe Asn Phe Arg Asp Pro Phe Thr Phe Glu Asp<br>                240                 245                 250 | | 1044 |
| ccc gcg cac ccc ggc gag act ttc atg gtt ttt gag ggc aac tcc gcc<br>Pro Ala His Pro Gly Glu Thr Phe Met Val Phe Glu Gly Asn Ser Ala<br>                255                 260                 265 | | 1092 |
| atg cag cgc gag acg gcg acc tgc aat gag gcc gac ctc ggc tac cgc<br>Met Gln Arg Glu Thr Ala Thr Cys Asn Glu Ala Asp Leu Gly Tyr Arg<br>270                 275                 280 | | 1140 |
| cag ggc gat ccg tac gcc gag acc gtc gac gat gtc aac gct tcc ggc<br>Gln Gly Asp Pro Tyr Ala Glu Thr Val Asp Asp Val Asn Ala Ser Gly<br>285                 290                 295                 300 | | 1188 |
| gcg acc tac cag atc ggg aac gtg ggt ctc gcg aag gcg aag aac aag<br>Ala Thr Tyr Gln Ile Gly Asn Val Gly Leu Ala Lys Ala Lys Asn Lys<br>                305                 310                 315 | | 1236 |
| caa ctg acg gag tgg gag ttc ctc ccg ccg atc ctg tcc gcg aac tgc<br>Gln Leu Thr Glu Trp Glu Phe Leu Pro Pro Ile Leu Ser Ala Asn Cys<br>                320                 325                 330 | | 1284 |
| gtt aca gac cag acc gag cgg ccg cag atc tac ttc aag gat ggt aag<br>Val Thr Asp Gln Thr Glu Arg Pro Gln Ile Tyr Phe Lys Asp Gly Lys<br>                335                 340                 345 | | 1332 |
| tcg tac ctc ttc acg atc agc cac cgc ggc acg ttc gcg gcg gga ctc<br>Ser Tyr Leu Phe Thr Ile Ser His Arg Gly Thr Phe Ala Ala Gly Leu<br>350                 355                 360 | | 1380 |
| gat ggc cct gag ggc gta tac gga ttc gtc ggc gac ggt atc cgc agc<br>Asp Gly Pro Glu Gly Val Tyr Gly Phe Val Gly Asp Gly Ile Arg Ser<br>365                 370                 375                 380 | | 1428 |
| gac tac cag ccc ctc aac ggc gga tcg ggc ctt gcc ctc ggc aac ccg<br>Asp Tyr Gln Pro Leu Asn Gly Gly Ser Gly Leu Ala Leu Gly Asn Pro<br>                385                 390                 395 | | 1476 |
| acg aac ctg aac ttc ttg ggc ggg cag ccg ttc gcc cct gac ttc aat<br>Thr Asn Leu Asn Phe Leu Gly Gly Gln Pro Phe Ala Pro Asp Phe Asn<br>                400                 405                 410 | | 1524 |

-continued

| | |
|---|---|
| cag cac ccg ggg cac ttc cag gcg tac tcc cac tac gtc atg ccc ggc<br>Gln His Pro Gly His Phe Gln Ala Tyr Ser His Tyr Val Met Pro Gly<br>        415                        420                        425 | 1572 |
| ggc ctt gtc cag tcg ttc atc gac acc atc gga acg cac gat gac ttc<br>Gly Leu Val Gln Ser Phe Ile Asp Thr Ile Gly Thr His Asp Asp Phe<br>430                          435                        440 | 1620 |
| gtt cgc ggc ggc acg ctc gca ccg acg gtg aaa atg gac atc ggc gtc<br>Val Arg Gly Gly Thr Leu Ala Pro Thr Val Lys Met Asp Ile Gly Val<br>445                        450                          455                  460 | 1668 |
| ggg ggc gac ccg acc aag acg gcc gtc gac tac tcg tac ggc agc gag<br>Gly Gly Asp Pro Thr Lys Thr Ala Val Asp Tyr Ser Tyr Gly Ser Glu<br>                      465                        470                        475 | 1716 |
| ggg ctg ggc ggc tgg gcg gat atc ccg gcg aac aag cac ctg ttc aca<br>Gly Leu Gly Gly Trp Ala Asp Ile Pro Ala Asn Lys His Leu Phe Thr<br>                480                        485                        490 | 1764 |
| aac ggc aag ttc ggc gtg gcg gtc tcc gac gag gcg gcg cag aag atc<br>Asn Gly Lys Phe Gly Val Ala Val Ser Asp Glu Ala Ala Gln Lys Ile<br>495                        500                          505 | 1812 |
| cgc aag atc ctc ggc tcg aag ttc gac gac tac ctc gac ggc gag ccc<br>Arg Lys Ile Leu Gly Ser Lys Phe Asp Asp Tyr Leu Asp Gly Glu Pro<br>510                        515                        520 | 1860 |
| gtc tca gcc acg gtg cga gcc ctc atc gag aag ctg ctg gca caa tac<br>Val Ser Ala Thr Val Arg Ala Leu Ile Glu Lys Leu Leu Ala Gln Tyr<br>525                        530                          535                  540 | 1908 |
| ggc ggc tga<br>Gly Gly | 1917 |

<210> SEQ ID NO 2
<211> LENGTH: 578
<212> TYPE: PRT
<213> ORGANISM: Arthrobacter sp.

<400> SEQUENCE: 2

Met Thr His Ser Thr Arg Gly Arg Val Arg Val Leu Ala Gly Gly
 1               5                  10                  15

Leu Ala Thr Ser Thr Leu Ala Ala Val Leu Ile Ala Gly Ala Ala
                20                  25                  30

Pro Ala Thr Ala Gln Ser Gly Leu Gln Asp Gly Pro Glu Pro Thr Ile
                35                  40                  45

His Thr Gln Gln Ala Tyr Ala Pro Glu Asp Asp Phe Thr Ala Lys Trp
     50                  55                  60

Thr Arg Ala Asp Ala Arg Gln Leu Gln Arg Met Ser Asp Pro Thr Ala
 65                  70                  75                  80

Pro Ser Arg Glu Asn Ser Met Pro Ala Ser Val Thr Met Pro Thr Val
                85                  90                  95

Pro Gln Asp Phe Pro Asp Met Ser Asn Glu Gln Val Trp Val Trp Asp
                100                 105                 110

Thr Trp Pro Leu Thr Asp Glu Asp Ala Asn Gln Tyr Ser Val Asn Gly
            115                 120                 125

Trp Glu Ile Ile Phe Ser Leu Val Ala Asp Arg Asn Leu Gly Phe Asp
        130                 135                 140

Asp Arg His Val Phe Ala Lys Ile Gly Tyr Phe Tyr Arg Pro Ala Gly
145                 150                 155                 160

Val Pro Ala Ala Glu Arg Pro Glu Asn Gly Gly Trp Thr Tyr Gly Gly
                165                 170                 175

Leu Val Phe Lys Glu Gly Val Thr Gly Gln Ile Phe Glu Asp Gln Ser
                180                 185                 190

-continued

Phe Ser His Gln Thr Gln Trp Ser Gly Ser Ala Arg Val Ser Lys Asn
        195                 200                 205

Gly Glu Ile Lys Leu Phe Phe Thr Asp Val Ala Phe Tyr Arg Asn Ser
    210                 215                 220

Asp Gly Thr Asn Ile Lys Pro Tyr Asp Pro Arg Ile Ala Leu Ser Val
225                 230                 235                 240

Gly Lys Val Lys Ala Asn Lys Lys Gly Val Thr Leu Thr Gly Phe Asn
                245                 250                 255

Lys Val Thr Asp Leu Leu Gln Ala Asp Gly Thr Tyr Tyr Gln Thr Gly
            260                 265                 270

Ala Gln Asn Glu Phe Phe Asn Phe Arg Asp Pro Phe Thr Phe Glu Asp
        275                 280                 285

Pro Ala His Pro Gly Glu Thr Phe Met Val Phe Glu Gly Asn Ser Ala
    290                 295                 300

Met Gln Arg Glu Thr Ala Thr Cys Asn Glu Ala Asp Leu Gly Tyr Arg
305                 310                 315                 320

Gln Gly Asp Pro Tyr Ala Glu Thr Val Asp Asp Val Asn Ala Ser Gly
                325                 330                 335

Ala Thr Tyr Gln Ile Gly Asn Val Gly Leu Ala Lys Ala Lys Asn Lys
            340                 345                 350

Gln Leu Thr Glu Trp Glu Phe Leu Pro Pro Ile Leu Ser Ala Asn Cys
        355                 360                 365

Val Thr Asp Gln Thr Glu Arg Pro Gln Ile Tyr Phe Lys Asp Gly Lys
    370                 375                 380

Ser Tyr Leu Phe Thr Ile Ser His Arg Gly Thr Phe Ala Ala Gly Leu
385                 390                 395                 400

Asp Gly Pro Glu Gly Val Tyr Gly Phe Val Gly Asp Gly Ile Arg Ser
                405                 410                 415

Asp Tyr Gln Pro Leu Asn Gly Gly Ser Gly Leu Ala Leu Gly Asn Pro
            420                 425                 430

Thr Asn Leu Asn Phe Leu Gly Gly Gln Pro Phe Ala Pro Asp Phe Asn
        435                 440                 445

Gln His Pro Gly His Phe Gln Ala Tyr Ser His Tyr Val Met Pro Gly
    450                 455                 460

Gly Leu Val Gln Ser Phe Ile Asp Thr Ile Gly Thr His Asp Asp Phe
465                 470                 475                 480

Val Arg Gly Gly Thr Leu Ala Pro Thr Val Lys Met Asp Ile Gly Val
                485                 490                 495

Gly Gly Asp Pro Thr Lys Thr Ala Val Asp Tyr Ser Tyr Gly Ser Glu
            500                 505                 510

Gly Leu Gly Gly Trp Ala Asp Ile Pro Ala Asn Lys His Leu Phe Thr
        515                 520                 525

Asn Gly Lys Phe Gly Val Ala Val Ser Asp Glu Ala Ala Gln Lys Ile
    530                 535                 540

Arg Lys Ile Leu Gly Ser Lys Phe Asp Asp Tyr Leu Asp Gly Glu Pro
545                 550                 555                 560

Val Ser Ala Thr Val Arg Ala Leu Ile Glu Lys Leu Leu Ala Gln Tyr
                565                 570                 575

Gly Gly

<210> SEQ ID NO 3
<211> LENGTH: 9
<212> TYPE: PRT

<213> ORGANISM: Arthrobacter sp.

<400> SEQUENCE: 3

Gln Ser Gly Leu Gln Asp Gly Pro Glu
 1               5

<210> SEQ ID NO 4
<211> LENGTH: 10
<212> TYPE: PRT
<213> ORGANISM: Arthrobacter sp.

<400> SEQUENCE: 4

Glu Ala Asp Leu Gly Tyr Arg Gln Gly Asp
 1               5                   10

<210> SEQ ID NO 5
<211> LENGTH: 9
<212> TYPE: PRT
<213> ORGANISM: Arthrobacter sp.
<220> FEATURE:
<223> OTHER INFORMATION: Xaa at postion 7 is any amino acid

<400> SEQUENCE: 5

Glu Trp Glu Phe Leu Pro Xaa Ile Leu
 1               5

<210> SEQ ID NO 6
<211> LENGTH: 10
<212> TYPE: PRT
<213> ORGANISM: Arthrobacter sp.

<400> SEQUENCE: 6

Glu Gln Val Trp Val Trp Asp Thr Trp Pro
 1               5                   10

<210> SEQ ID NO 7
<211> LENGTH: 20
<212> TYPE: DNA
<213> ORGANISM: Arthrobacter sp.

<400> SEQUENCE: 7
ggsctscagg acggsccsga                                                  20

<210> SEQ ID NO 8
<211> LENGTH: 20
<212> TYPE: DNA
<213> ORGANISM: Arthrobacter sp.

<400> SEQUENCE: 8
ctcgtccasa cccasaccct                                                  20

<210> SEQ ID NO 9
<211> LENGTH: 221
<212> TYPE: DNA
<213> ORGANISM: Arthrobacter sp.

<400> SEQUENCE: 9
gggctccagg acggcccgga gccgacaatt cacactcagc aggcgtacgc ccccgaggat      60
gatttcaccg ccaagtggac acgcgccgac gcccgccagt tgcagcgcat gtccgacccc     120
accgcgccgt cgcgcgagaa ctcgatgccg gcgtccgtca ccatgccaac tgtgccgcag     180
gacttcccgg acatgtccaa cgagcaggtg tgggtgtggg a                         221